United States Patent
D'Amato et al.

(10) Patent No.: US 7,109,187 B2
(45) Date of Patent: *Sep. 19, 2006

(54) ESTROGENIC COMPOUNDS AS ANTI-MITOTIC AGENTS

(75) Inventors: Robert John D'Amato, Lancaster, PA (US); Moses Judah Folkman, Brookline, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/780,650

(22) Filed: Feb. 12, 2001

(65) Prior Publication Data

US 2003/0236408 A1 Dec. 25, 2003

Related U.S. Application Data

(63) Continuation of application No. 09/436,610, filed on Nov. 9, 1999, now abandoned, which is a continuation of application No. 09/243,158, filed on Feb. 2, 1999, now abandoned, which is a division of application No. 08/838,699, filed on Apr. 25, 1997, now Pat. No. 5,892,069, which is a division of application No. 08/571,265, filed on Dec. 12, 1995, now Pat. No. 5,661,143, which is a continuation of application No. 08/102,767, filed on Aug. 6, 1993, now Pat. No. 5,504,074.

(51) Int. Cl.
*A61K 31/56* (2006.01)

(52) U.S. Cl. ............... 514/182; 514/824; 514/825; 514/863; 514/886; 514/899; 514/912; 514/914

(58) Field of Classification Search .......... 514/182, 514/824, 825, 863, 886, 899, 912, 914
See application file for complete search history.

(56) References Cited

U.S. PATENT DOCUMENTS

| | | |
|---|---|---|
| 2,584,271 A | 2/1952 | Huffman |
| 2,846,453 A | 8/1958 | Hoehn |
| 3,166,577 A | 1/1965 | Ringold et al. |
| 3,410,879 A | 11/1968 | Smith et al. |
| 3,470,218 A | 9/1969 | Farah |
| 3,492,321 A | 1/1970 | Crabbe |
| 3,496,272 A | 2/1970 | Kruger |
| 3,562,260 A | 2/1971 | De Ruggieri et al. |
| 3,956,348 A | 5/1976 | Hilscher |
| 4,172,132 A | 10/1979 | Draper et al. |
| 4,212,864 A | 7/1980 | Tax |
| 4,307,086 A | 12/1981 | Tax |
| 4,522,758 A | 6/1985 | Ward et al. |
| 4,552,758 A | 11/1985 | Murphy et al. |
| 4,634,705 A | 1/1987 | DeBernardis et al. |
| 4,743,597 A | 5/1988 | Javitt et al. |
| 4,808,402 A | 2/1989 | Leibovich et al. |
| 4,990,538 A * | 2/1991 | Harris et al. ........... 514/648 |
| 4,994,443 A | 2/1991 | Folkman et al. |
| 5,001,116 A | 3/1991 | Folkman et al. |
| 5,135,919 A | 8/1992 | Folkman et al. |
| 5,504,074 A * | 4/1996 | D'Amato et al. ........... 514/182 |
| 5,521,168 A | 5/1996 | Clark |
| 5,621,124 A | 4/1997 | Seilz et al. |
| 5,629,340 A | 5/1997 | Kuwano et al. |
| 5,639,725 A | 6/1997 | O'Reilly et al. |
| 5,643,900 A * | 7/1997 | Fotsis et al. ........... 514/182 |
| 5,661,143 A * | 8/1997 | D'Amato et al. ........... 514/182 |
| 5,716,981 A | 2/1998 | Hunter et al. |

(Continued)

FOREIGN PATENT DOCUMENTS

| | | |
|---|---|---|
| DE | 1907330 | 10/1969 |
| DE | 2 004 516 | 9/1970 |
| DE | 27 57 157 | 12/1977 |
| DE | 3625315 | 1/1988 |
| EP | 0166937 | 8/1968 |
| GB | 857080 | 12/1960 |
| GB | 857081 | 12/1960 |
| GB | 1570597 | 7/1980 |
| JP | 39-5480 | 3/1961 |
| JP | 41 000100 A | 1/1966 |

(Continued)

OTHER PUBLICATIONS

Getahun et al., Synthesis of Alkoxy–Substituted Diaryl Compounds and Correlation of Ring Separation with Inhibition of Tubulin Polymerization: Differential Enhancement of Inhibitory Effects Under Suboptimal Polymerization Reaction Conditions, *Journal of Medical Chemistry*, vol. 35 (6), pp. 1058–1067, Mar. 20, 1992.

Gross et al., Inhibition of Tumor Growth, Vascularization, and Collagenolysis in the Rabbit Cornea by Medroxyprogesterone, *Proceedings of the National Academy of Science USA*, vol. 78 (2), pp. 1176–1180, Mar. 1981.

Hartley–Asp et al., Diethylstilbestrol Induces Metaphase Arrest and Inhibits Microtubule Assembly, *Mutation Research*, vol. 143 (4), 231–235, Aug. 1985.

Huber et al., Tubulin Binding of Conformationally Restricted Bis–Aryl Compounds, *Bioorganic & Medicinal Chemistry Letters*, vol. 1 (5), pp. 243–246, 1991.

Lin et al., Interactions of Tubulin with Potent Natural and Synthetic Analogs of the Antimitotic Agent Combretastatin: A Structure–Activity Study, *Molecular Pharmacology*, vol. 34 (2), pp. 200–208, Aug. 1988.

(Continued)

*Primary Examiner*—Barbara P. Badio
(74) *Attorney, Agent, or Firm*—Kirkpatrick Stockton LLP

(57) ABSTRACT

The application discloses methods of treating mammalian diseases characterized by abnormal cell mitosis by administering estradiol derivatives including those comprising colchicine or combretastatin A-4 structural motifs of the general formulae found below in a dosage sufficient to inhibit cell mitosis. The application discloses novel compounds used in the methods.

14 Claims, 3 Drawing Sheets

U.S. PATENT DOCUMENTS

| | | |
|---|---|---|
| 5,733,876 A | 3/1998 | O'Reilly et al. |
| 5,763,432 A | 6/1998 | Tanabe et al. |
| 5,776,704 A | 7/1998 | O'Reilly et al. |
| 5,792,845 A | 8/1998 | O'Reilly et al. |
| 5,837,682 A | 11/1998 | Folkman et al. |
| 5,854,205 A | 12/1998 | O'Reilly et al. |
| 5,854,221 A | 12/1998 | Cao et al. |
| 5,861,372 A | 1/1999 | Folkman et al. |
| 5,885,795 A | 3/1999 | O'Reilly et al. |
| 5,892,069 A | 4/1999 | D'Amato et al. |
| 5,958,892 A | 9/1999 | Mukhopadhyay et al. |
| 6,011,023 A | 1/2000 | Clark et al. |
| 6,011,024 A | 1/2000 | Reed et al. |
| 6,046,186 A | 4/2000 | Tanabe et al. |
| 6,054,598 A | 4/2000 | Sachdeva et al. |
| 6,136,992 A | 10/2000 | Ram et al. |
| 6,200,966 B1 | 3/2001 | Stewart |
| 6,239,123 B1 | 5/2001 | Green |
| 6,284,789 B1 | 9/2001 | LaLonde et al. |
| 6,358,940 B1 | 3/2002 | Conney |
| 6,399,773 B1 | 6/2002 | Liu et al. |
| 6,410,029 B1 | 6/2002 | Mukhopadhyay et al. |
| 6,514,971 B1 | 2/2003 | Thomas et al. |
| 6,528,676 B1 | 3/2003 | D'Amato et al. |
| 6,605,622 B1 | 8/2003 | Green et al. |

FOREIGN PATENT DOCUMENTS

| | | |
|---|---|---|
| JP | 42-928 | 1/1967 |
| JP | 58-131978 | 8/1983 |
| JP | 63090763 A | 4/1988 |
| JP | 63-119500 | 5/1988 |
| JP | 1240038 A1 | 10/1996 |
| JP | 11-209322 | 8/1999 |
| WO | WO 87/02367 A3 | 4/1987 |
| WO | WO 88/08002 A1 | 10/1988 |
| WO | WO 90/15816 A1 | 12/1990 |
| WO | WO 93/03729 | 3/1993 |
| WO | WO 93/19746 A1 | 10/1993 |
| WO | WO 95/04535 A1 | 2/1995 |
| WO | WO 98/32763 A1 | 7/1998 |
| WO | WO 98/40398 | 9/1998 |
| WO | WO 99/01142 A1 | 1/1999 |
| WO | WO 99/22728 A1 | 5/1999 |
| WO | WO 99/33858 A3 | 7/1999 |
| WO | WO 99/33859 A2 | 7/1999 |
| WO | WO 99/35150 A3 | 7/1999 |
| WO | WO 00/07576 A2 | 2/2000 |
| WO | WO 00/10552 A3 | 3/2000 |

OTHER PUBLICATIONS

Lincoln et al., Conformation of Thiocolchicine and Two B–Ring–Modified Analogues Bound to Tubulin Studied with Optical Spectroscopy, *Biochemistry*, vol. 30 (5), pp. 1179–1187, Feb. 5, 1991.

Lottering et al., Effects of the 17β–Estradiol Metabolites on Cell Cycle Events in MCF–7 Cells (Chemical Abstracts Doc. No: 117:245769, 1992), *Cancer Research*, vol. 52, pp. 5926–5932, Nov. 1, 1992.

*Research Plus Catalog*, pp. 50–58, 1993.

U.S. patent application No. 09/641,327 filed Aug. 18, 2000, entitled "Antiangiogenic Agents".

U.S. patent application No. 09/779,331 filed Feb. 8, 2001 entitled "Antiangiogenic Agents".

U.S. patent application No. 10/077,142 filed Feb. 15, 2002 entitled "Estrogenic Compounds as Anti–Mitotic Agents".

U.S. patent application No. 09/866,279 filed May 25, 2001 entitled "Use of Estrogenic Compounds as Anti–Fungal Agents".

U.S. patent application No 09/899,702 filed Jul. 5, 2001 entitled "Estrogenic Compounds as Antiangiogenic Agents".

U.S. patent application No. 09/939,208 filed Aug. 24, 2001 entitled "Antiangiogenic Agents".

Adams, E.F. et al., Steroidal regulation of oestradiol–17B dehydrogenase activity of the human breast cancer cell line MCF–7 (Chemical Abstracts Doc. No. 109:32325, 1988), *Journal of Endocrinology*, vol. 188 (1) pp. 149–154, Jul. 1988.

Bhat et al., Estradiol–induced Mitotic Inhibition in the Bursa of Fabricius of Male Domestic Duckling (Chemical Abstracts Doc. No: 98:31837, 1982), *Mikroskopie*, vol. 39 pp. 113–117 May 1982.

Blickenstaff et al., Estrogen–Catharanthus (Vinca) Alkaloid Conjugates (Chemical Abstracts Doc. No: 94:114277, 1981), *Cytotoxic Estrogens in Hormone Receptive Tumors*, pp. 89–105 1980.

Boye et al., 185. Deaminocolchinyl Methyl Ether: Synthesis from 2,3,4,4'–Tetramethoxybiphenyl–2–carbaldehyde. Comparison of Antitubulin Effects of Deaminocolchinyl, *Helvetica Chimica Acta*, vol. 72, pp. 1690–1696, 1989.

Crum, R. et al., A New Class of Steroids Inhibits Angiogenesis in the Presence of Heparin or a Heparin Fragment, *Science*, vol. 230, pp. 1375–1378, Dec. 20, 1985.

Evans et al., A Convergent Total Synthesis of (+)– Colchicine and (+)– Desacetamidoisocolchicine, *Journal of the American Chemical Society*, vol. 103, pp. 5813–5821, Sep. 23, 1981.

Fitzgerald, Molecular Features of Colchicine Associated with Antimitotic Activity and Inhibition of Tubulin Polymerization, *Biochemical Pharmacology*, vol. 25, pp. 1383–1387, Jun. 15, 1976.

Morgan et al., Calcium and Oestrogen Interactions upon the Rat Thymic Lymphocyte Plasma Membrane (Chemical Abstracts Doc. No: 85:172052, 1976), *Biochemical and Biophysical Research Communications*, vol. 72 (2), pp. 663–672, Sep. 20, 1976.

Mukundan et al., Liver Regeneration in Oral Contraceptive Treated Female Rats—Effects of Moderate Malnutrition (Chemical Abstracts Doc. No: 102:143342, 1984), *Hormone and Metabolic Research*, vol. 16 (12), pp. 641–645, Dec. 1984.

Nakamura et al., Studies on the Total Synthesis of dl–Colchicine. I. Synthesis of 3–Hydroxy–9, 10, 11–trimethoxy–1,2,3,4,6,7–hexahydro–5H–dibenso[a,c] cycloheptatrien–5–one, *Chemical and Pharmaceutical Bulletin*, vol. 10, pp. 281–290, 1962.

Oppolzer et al. 177., The Enantioselective Synthesis of (+)–Estradiol from 1,3–Dihydrobenzo[c]thiophene–2,2–dioxide by Successive Thermal $SO_2$ –Extrusion and Cycloaddition Reactions, *Helvetica Chimica Acta*, vol. 63, pp. 1703–1707, 1980.

Paull et al., Identification of Novel Antimitotic Agents Acting at the Tubulin Level by Computer–assisted Evaluation of Differential Cytotoxicity Data, *Cancer Research*, vol. 52, pp. 3892–3900, Jul. 15, 1992.

Poli et al., Tumor Necrosis Factor α Functions in an Autocrine Manner in the Induction of Human Immunodeficiency Virus Expression, *Proceedings of the National Academy of Science USA*, vol. 87, pp. 782–785, Jan. 1990.

Rao et al., Structural Specificity of Estrogens in the Induction of Mitotic Chromatid Non–Disjunction in Hela Cells, *Experimental Cell Research*, vol. 48, pp. 71–81, 1967.

Ravindra, R., Effect of Estradiol on the in vitro Assembly of Rat Brain Tubulin, *Journal of Indian Institute of Science*, vol. 64 (3), pp. 27–35, Mar. 1983.

Sakakibara et al., Effects of Diethylstilbestrol and its Methl Ethers on Aneuploidy Induction and Microtubule Distribution in Chinese Hamster V79 cells, *Mutation Research*, vol. 263, pp. 269–276, Aug. 1991.

Sato et al., Effect of Estradiol and Ethynylestradiol on Microtubule Distribution in Chinese Hamster V79 Cells, *Chemical and Pharmaceutical Bulletin*, vol. 40 (1), pp. 182–184, Jan. 1992.

Sato et al., Disruptive Effect of Diethylstilbestrol on Microtubules, *Gann*, vol. 75, pp. 1046–1048, Dec. 1984.

Sawada et al., Colchicine–Like Effect of Diethylstilbestrol (DES) on Mammalian Cells in Vitro, *Mutation Research*, vol. 57, pp. 175–182, May 1978.

Seegers et al., Cyclic–AMP and Cyclic–GMP Production in MCF–7 Cells Exposed to Estradiol–17 Beta, Catecholestrogens and Methoxy–Estrogens in MCF–7 Cells (Meeting Abstract only), *Joint MCI–1st Symposium. Third 1st International Symposium. Biology and Therapy of Breast Cancer*, Sep. 25, 1989.

Seegers, J.C. et al., The Cytotoxic Effects of Estradiol–17B, Catecholestradiols and Methoxyestradiols on Dividing MCF–7 and HeLa Cells, *Journal of Steroid Biochemistry*, vol. 32 (6), pp. 797–809, 1989.

Sharp et al., Diethylstilbestrol: the Binding and Effects of Diethylstilboestrol upon the Polymerisation and Depolymerisation of Purified Microtubule Protein in vitro, *Carcinogens*, vol. 6 (6), pp. 865–871, Jun. 1985.

Spicer et al., Catecholestrogens Inhibit Proliferation and DNA Synthesis of Porcine Granulosa Cells in Vitro: Comparison with Estradiol, 5α–dihydrotestosterone, Gonadotropins and Catecholamines (Chemical Abstracts Doc. No:, *Molecular and Cellular Endocrinology*, vol. 64, pp. 119–126, 1989.

Sternlicht et al., Colchicine Inhibition of Microtubule Assembly via Copolymer Formation, *The Journal of Biological Chemistry*, vol. 254 (20), pp. 10540–10550, Oct. 25, 1979.

Sun et al., Antitumor Agents. 139. Synthesis and Biological Evaluation of Thiocolchicine Analogs 5,6–Dihydro–6(S)–(acyloxy)–and 5,6–Dihydro–6(S)–(acyloxy)methyl–1,2, 3–trimethoxy–9–(methylthio)–8H–cyclohepta[a]naphthalene–8–ones as Novel Cytotoxic, *Journal of Medicinal Chemistry*, vol. 36, pp. 544–551, Mar. 5, 1993.

Sunagawa et al., Synthesis of Colchicine; Synthesis of dl–'Demethyoxydeoxy–hexahydrocolchicine, *Chemical & Pharmaceutical Bulletin*, vol. 9, pp. 81–83, 1961.

Tsutsui et al., Comparison of Human Versus Syrian Hamster Cells in Culture for Induction of Mitotic Inhibition, Binucleation and Multinucleation, Following Treatment with Four Aneuploidogens, *Toxicology in Vitro*, vol. 4 (1), pp. 75–84, 1990.

Van Tamelen et al., The Synthesis of Colchicine, *Tetrahedron*, vol. 14, pp. 8–34, Sep. 1961.

Wheeler et al., Mitotic Inhibition and Aneuploidy Induction by Naturally Occurring and Synthetic Estrogens in Chinese Hamster Cells in Vitro, *Mutation Research*, vol. 171, pp. 31–41, 1986.

Wheeler et al., Mitotic Inhibition and Chromosomes Displacement Induced by Estradiol in Chinese Hamster Cells (Chemical Abstracts Doc. No: 105:54822, 1986), *Cell Motility and the Cytoskeleton*, vol. 7 (3), pp. 235–247, 1987.

Schumacher et al., "The physiological estrogen metabolite of 2–methoxyestradiol reduces tumor growth and induces apoptosis in human solid tumors."J. Cancer Res. Clin. Oncol., vol. 127, pp. 405–410, 2001.*

Probluda et al., "2–Methoxyestradiol: An endogenous antiangiogenic and antiproliferative drug candidate."Cancer and Metastasis Reviews, vol. 19, pp. 173–179, 2000*

Seegers et al., "The cytotoxic effects of estradiol–17beta, catecholestradiols and methoxyestradiols on dividing MCF–7 and HeLa cells."J. Steroid Biochem., vol. 32(6), pp. 797–809, 1989.*

Gian Tondury et al., Zur Wirkung Der Sexualhormone Auf Wachstum und Differenzierung (See English Summary p. 55), *Cambridge Philosophical Society*, pp. 28–58, Dec. 17, 1955

Von Mollendorff, W., Wachstumsstorungen–durch–Geschlechtshormone, nach Untersuchungen an ewebekulturen, English Translation needed. PP. 187–202, Jun. 12, 1941.

Staples, et al., Structural Requirement for Steroid Inhibition of Sheep Lymphocytes Mitogenesis in vitro, *Steroids*, pp. 419–433, Nov. 1984.

Gian Tondury et al. Zur Wirkung Der Sexualhormone Auf Wachstum und Differenierung (See English Summary Page 55). *Cambridge Philosophical Society*vol/Iss: pp. 28–58 Dec. 17, 1955.

Staples et al. Structural Requirements for Steroid Inhibition of Sheep Lymphocyte Mitogenesis in vitro. *Steroids*vol/Iss: 44 (5) pp. 419–433 Nov. 1984.

Lilopristone/(1–[–4–(Dimethylamino)phenyl]–17–(3–hydroxy–1–propenyl)estra–4,9–diene–3–One; AK 98734. *Dictionary of Drugs*(1990), Dict. of Steroids (1991), Dict. of Org. Cmpds (6th Ed) (1996), Dict. of Pharm Agents(1997).

*The Merck Index*11th Edition, p. 88, 1989.

Registry No. 56933–77–8, *Chemical Abstracts*, 2003.

Registry No. 56933–78–9, *Chemical Abstracts*, 2003.

Registry No. 57380–15–1, Chemical Abstracts 2003.

Registry No. 71782–94–0, *Chemical Abstracts*, 2003

Registry No. 71782–95–1, *Chemical Abstracts*, 2003

Registry No. 101277–11–6, *Chemical Abstracts*, 2003.

News Article: Hoffman–La Roche Signs $70 Million Deal with Millenium on Genomics Technology, *Genetic Engineering News*, Apr. 15, 1994.

News Article: Advanced Drug Delivery Systems Peak Interest of Pharmaceutical & Biotech Firms, *Genetic Engineering News*Apr. 15, 1994.

News Article: Nasal Spray for Treating Bleeding Disorders, *Genetic Engineering News*, Apr. 15, 1994.

Synthesis and evaluation of uterotrophic and antiimplantation activities of 2–substituted estradiol derivatives. *Steroids*vol/Iss: 57, pp. 199–204, Apr. 1992.

Aizu–Yokota, et al. Natural Estrogens Induce Modulation of Microtubules in Chinese Hamster V79cells in culture. *Cancer Research*vol/Iss: 55, pp 1863–1868 May 1, 1995.

Algire, G.H. et al., Vascular reactions of normal and malignant tumors in vivo. I. Vascular reactions of mice to wounds and to normal and neoplastic transplants. *Journal of the National Cancer Institute*, vol/Iss: 6 pp. 73–85, Aug. 1945.

Alieve et al. 54929q Synthesis of cycloalkyl derivatives of dihydric phenols and their ethers. *Chemical Abstracts*vol/Iss: 72 p. 370 1970.

Anstead et al. The Estradiol Pharmacophore: Ligand Structure–Estrogen Receptor Binding Activity Relationships and a Model for the Receptor Binding Site. *Steroid*vol/Iss:62 pp. 268–303 1997.

Arnoldi et al. Sweet Isovanillyl Derivatives: Synthesis and Structure–Taste Relationships of Conformationally Restricted Analog (Abstract only). *Journal of Agric. Food Chem.*vol/Iss: 46(10) pp. 4002–4010 1998.

Attalla et al. 2–Methoxyestradiol Arrests Cells in Mitosis without Depolymerizing Tubulin *Biochemical and Biophysical Research Communications*vol. 228 pp. vol/Iss: 467–473 1996.

Attalla et al. 2–Methylestradiol–Induced Phosphorylation of Bcl–2: Uncoupling from JNK/SAPK Activation (Abstract only) *Biochemical and Biophysical Research Communicatioins*vol/Iss: 247 (3) pp. 616–619 Jun. 29, 1998.

Audier et al. Orientation de la Fragmentation en spectrometrie de masse par introduction de groupements fonctionnels. VIII. –Etheylenecetals de ceto 3 steroides. English translation needed. *Bulletin De La Societe Chemie De France*, vol/Iss: 10 pp.3088–3090 1965.

Ayala et al. The induction of Accelerate Thymic Programmed Cell Death During Polymicrobial Sepsis: Control by Corticosteroids but not Tumor Necrosis Factor (Abstract only). *Shock*vol/Iss: 3(4) pp. 259–267. Arp. 1955.

Banik et al. Orally Active Long–Acting Estrogen (AY–20, 121) (3–(2–propynyloxy)–estra–1,3,5, (10)–triene–17.beta.–ol trimethylacetate) Identifier only). *Steroids*vol/Iss: 16(3) pp. 289–296. 1970.

Bardon et al. Steroid Receptor–Mediated Cytotoxicity of an Antiestrogen and an Antiprogestin in Breast Cancer Cells (Abstract only). *Cancer Research*vol/Iss: 47 (5) pp. 1441–1448 Mar. 1, 1987.

Bindra et al. Studies in Antifertility Agents.8.Seco Steroids.3.4,6–Secoestradiol and Some Related Compounds *Journal of Medicinal Chemistry*vol/Iss: 18(9): pp. 921–925 1975.

Barnes et al. Tumor Necrosis Factor Production in Patients with Leprosy. *Infection and Immunity*pp. 1441–1446 Apr. 1992.

Blagosklonny et al. Raf–1/bcl–2 Phosphorylation: A Step from Microtubule Damage to Cell Death *Cancer Research*vol/Iss: 57 pp. 130–135 Jan. 10, 1997.

Blickenstaff et al. Synthesis of Some Analogs & Estradiol *Steroids*vol/Iss: 46(4,5) pp. 889–902 Oct. 1985.

Brandi et al. Bone endothelial cells as estrogn targets (Abstract only) *Calcif. Tissue Int.*53(5): pp. 312–317 1993.

Brem, H. et al. Interstitial chemotherapy with drug polymer implants for the treatment of recurrent gliomas. *Journal of Neurosurgery*74 pp. 441–446. Mar. 1, 1991.

Brodie, A.M. Aromatase Inhibitors in the Treatment of Breast Cancer (Abstract only). *Journal of Steroid Biochemistry and Molecular Biology*49(4–6) pp. 281–287. Jun. 1994.

Brosens et al. Comparative Study of the Estrogenic Effect of Ethinylestradiol and Mestranol on the Endometrium. *Laboratory for Gynecological Physiopathology*14(6): pp. 679–685 Dec. 1, 1976.

Burrows, N.P. Thalidomide Modifies Disease *British Medical Journal*307(6909) pp. 939–940 Oct. 9, 1993.

Cambie et al. Aromatic Steroids. Part II. Chromium Trioxide Oxidation of Some Oesrtra–1,3–5(10)–trienes 9 pp. 1234–1240 1969.

Cambie et al. Aromatic Steroids. Part I. Oxidation Products of 3–Melhoxyestra–1,3,5(10)–triene–17α–yl Acetate. *J. Chem. Soc.*pp. 2603–2608 1968.

Castagnetta, L. et al. Simple Approach to Measure Metabolic Pathways of Steroids in Living Cells. *Journal of Chromatography*vol/Iss: 572. pp. 25–39 Dec. 6, 1991.

Chasserot–Golaz et al. Biotransformation of 17.beta.–hydroxy–11.beta.–(4–dimethylaminophenyl) 17.alpha.1–propynyl–estra–4,9–diene–3–one 9RU486) in Rat Hepatoma Variants (Identifier only). *Biochemical Pharmacology*vol/Iss: 46(11) pp. 2100–2103 1993.

Chen et al. A New Synthetic Route to 2–and 4–Methoxyestradiols by ucleophili Substitution *Steroids*vol/Iss: 47(1) pp. 63–66 Jan. 1986.

Chen et al. Synthesis of 11.beta.–(4–dimethylaminophenyl)–17.beta–hydroxy–17.alpha.–(1–propynyl)estra–4,9–dien–3–one (RU486) (Identifier only) *Nanjing Yaoxueyaun Xuebao*vol/Iss: 17(4) pp. 282–285 1986.

Collins et al. The Structure and Function of Estrogens. XI. Synthesis of (+/−)–7(8–11a) abeo–Estradiol and its 9,11–Didehydro Derivative. *Aust. Journal of Chemistry*vol/Iss: 45(1) pp. 71–97 1992.

Corey et al. The Structure of N,N–Dimethylhydrazones to Synthesis. Use in Efficient, Positionally and Stereochemically Selective C–C Bond Formation; Oxidative Hydrolysis to Carbonyl Compounds *Tetrahedron Letters*vol/Iss: 1 pp. 3–6 1976.

Corey et al. Facile Conversion of N,N–Dimethylhydrazones to Cabonyl Compounds by Cupric Ion–Catalyzed Hydrolysis *Tetrahedron Letters*vol/Iss: vol. 41 pp. 36678–3668 1976.

Crabbe, P. Cotton effect of the styrene Chromophore (Abstract only) *Chem. Ind.*vol. /Iss: 27 pp. 917–918 1969.

Cummings et al. Apoptosis *The American Journal of Surgical Pathology*vol/Iss: 21(1)pp. 88–101 1997.

Cushman et al. Synthesis, Antitubulin and Antimitotic Activity, and Cytotoxicity of Analogs of 2–Methoxyestradiol, and Endogenous Mammalian Metabolite of Estradiol that Inhibits Tubulin Polymerization by Binding to the Colchicine Binding Site *Journal of Medicinal Chemistry*vol/Iss: 38(12) pp. 2041–2049 Jun. 9, 1995.

Cushman et al. Synthesis of Analog of 2–Methoxyestradiol with Enhanced Inhibitory Effects on Tubulin Polymerization and Cancer Cell Growth *Journal of Medicinal Chemistry*vol/Iss: 40(15) pp. 2323–2334.

D'Amato et al. 2–Methoxyestradiol, an Endogenous Mammalian Metabolite, Inhibits Tubulin Polymerization by Interactiing at the Colchicine Site *Proceedings of the National Academy of Science USA*vol. /Iss: 91 pp. 3964–3968 Apr. 26, 1994.

D'Amato, R.J. et al. Thalidomide is an inhibitor of Angiogenesis *Proceeding of the National Academy of Sciences USA*vol/Iss: 91 pp. 4082–4085 Apr. 1, 1994.

Ding et al. Sex Hormone–Binding Globulin Mediates Prostate Androgen Receptor Action via a Novel Signaling Pathway (Abstract only). *Endocrinology*vol/Iss: 139(1) pp. 213–218 1998.

Durani et al. Seco–Oesradiols and Some Non–Steroidal Oestrogens: Structural Correlates of Oestrogenic Action. *Journal of Steroid Biochemistry*vol/Iss: 11 ppl. 67–77 1979.

DVIR et al. Thin–Layer Chromatography of DANSY-L–oestrogens *Journal of Chromatography*vol/Iss. 52 pp. 505–506 Nov. 4, 1970.

Eder et al. Synthesis of von Ostradiol (in German –No translation available) *Chem. Br.*English Abstract only. vol./Iss: 109 1976. pp. 2948–2953 1976.

El–Tombary. Synthesis, Uterotropic, And Antiuterotrophic Activities for Some Estradiol Derivatives Containing Thiadiazole, Thiazolaine, and Thiazolidinone Moieties. *Arch. Pharm. Pharm. Med. Chem.*vol./Iss: 330 (9–10) pp. 295–302. 1997

Emons et al. Modulation der hypophysaren Sekretion von Luteinisierendem Hormon (LH) durch Ostrogene *Focus MHL*English Abstract only. vol./Iss: 3 pp. 221–228. 1986.

Epe et al. Microtubular Proteins as Cellular Targets for Carcinogenic Estrogens and Other Carcinogens. *Mechanisms of Chromosomes Distribution and Aneuploidy*pp. 345–351. 1989.

Fanchenko et al. Characteristics of the guinea pig uterus estrogen receptor system (Abstract only) *Byull. Eksp. Biol. Med.*vol./Iss: 85(4) pp. 467–470 1978.

Fetizon et al. Synthesis of 2–keto steroids (Abstract only) *Bull. Soc. Chim. FR.*vol./Iss: 8 pp. 3301–3306 1968.

Fevig et al. A Short, Stereoselective Route to 16β(Substituted–alkyl)estradiol Derivatives. *Journal of Organic Chemistrry*vol./Iss: 52 pp. 247–251 1987.

Field et al. Effect of Thalidomide on the Graft versus Host Reaction. *Nature*vol./Iss: 211 (5055) pp. 1308–1310. Sep. 17, 1966.

Fieser et al. N–Methylformanilide. *Organic Synthesis Collective Volume 3*vol./Iss: 3 pp. 590–591 1955.

Fishman, J. Synthesis of 3–Methoxyestrogens. *Journal of the American Chemical Society*vol./Iss: 80 pp. 1213–1216 Mar. 5, 1998.

Flohe et al. Studies on the Hypothetical Relationship of Thalidomide–induced Embryopathy and Collagen Biosynthesis. *Arzeimitte/Forschung*(Germany West) vol./Iss: 31(2) pp. 315–320 Jan. 1, 1981.

Folkman et al. Angiogenesis Inhibition and Tumor Regression Causd by Heparin or a Heparin Fragment in the Presence of Cortisone. *Sciene*vol./Iss: 285 (21) pp. 1182–1186 Nov. 18, 1971.

Folkman, J. Tumor Angiogenesis: Therapeutic Implications. *New England Journa of Medicine*vol./Iss: 285 (12) pp. 1182–1186 Nov. 18, 1971.

Folkman, J. et al. Induction of Angiogenesis During the Transition from Hyperplasia to Neolasia *Nature*vol./Iss: 339 May 4, 1989.

Folkman, J. et al. Tumor Behavior in Isolated Perfused Organs in vitro Growth and Metastases of Biopsy Material in Rabbit Thyroid and Canine Intestinal Segment. *Annals of Surgery*vol./Iss: 164(3) pp. 491–502 Sep. 1, 1956.

Fotsis et al. The Endogenous Oestrogen Metabolite 2–Methoxyoestradiol Inhibits Angiogenesis and Suppresses Tumour Growth *Nature*vol./Iss: 368pp. 237–239 Mar. 17, 1994.

Gadosy et al. Generation, Characterization, and Deprotomtaion of Phenol Radical Cations. *Journal of Physical Chemistry*vol./Iss: 103 pp. 8834–8839 1999.

Gandhi et al. Mannich Reaction of Estrone *Journal of Indian Chem. Soc.*Abstract Only vol./Iss: 39 pp. 306–308 1962.

Gaslini et al. Reaction of Eugenol with Syntheis Gas. Synthesis of 5,6,7–8–Tetrahydro–3–methoxy–2–napthol. *Journal of Organic Chemistry*vol./Iss: 29(5) pp. 1177–1180 May 1964.

Gimbrone, M.A. et al. Tumor Growth and Neovascularization: An Exprimental Model Using the Rabbit. *Journal of the National Cancer Institute*vol./Iss: 52(2) pp. 413–427 Feb. 1974.

Gimbrone, M.A. et al. Tumor dormancy *in vivo*by Prevention of Neovascularization. *Journal of Experimental Medicine*vol./Iss: 136 pp. 261–176 1972.

Gonzalez, et al. Synthesis and Pharmacological Evaluation of 8αEstaduik Derivatives. *Steroids*vol./Iss: 40 (2) pp. 171–187 Sep. 1982.

Gross, L.J. et al. Modulation of Solid Tumor Growth in vivo by bFGF (Abstract only). *Proceedings of the American Association of Cancer Research*vol./Iss: 31 p. 79 Mar. 1990.

Gujjar et al. The Effect of Estradiol. on *Candida albicans*-Growth. *Annals of Clinical and Laboratory Science*vol./Iss: 27 (2) pp. 151–156 1997.

Gunzler, V. Thalidomide–A Therapy for the Immunological Consequences of HIV Infection?*Medical Hypothesis*vol./Iss: 30 (2) pp. 105–109. Oct. 1989.

Gupta et al. Antifertility Agents. XIV. Secosteroids. VII. Synthesis of 2αand 2β, 6β–dimethyl–3β–(p–hyphenyl)–trans–bicyclo[4.3.0] nonan–7–ones and some related compounds (Abstract only). *Indian Journal of Chemistry*vol./Iss: 13(7) pp. 759–760 1975.

Gupta et al. Studies in Antifertility Agents. Part XVIII. 2α6β–Diethyl–3β–(p–hydroxyphenyl)–trans–bicyclo[4.3.0] nonan–7β–ol and 6β–methyl–3β(p–hydroxyphenyl)–2α–propyl–transbicyclo [4.3.0]nonan–7β–ol (Abstract only). *Indian Journal of Chemstry*Abstract only. vol./Iss: 19B (10) pp. 886–890. 1980.

Gutierrez–Rodriguez et al. Treatment of Refractory Rheumatoid Arthritis –The Thalidomide Experience. *The Journal of Rheumatology*vol./Iss: 16 (2) pp. 158–163 Feb. 1989.

Hahnel et al. The Specificity of the Estrogen Recepto of Human Uterus. *Journal of Steroid Biochemistry*vol./Iss: 4 pp. 21–31 1973.

Haldar et al. Bc12 iis the Guardian of Microtubule Integrity. *Cancer Res.*vol./Iss: 57 pp. 229–233 Jan. 15, 1997.

Hamel et al. Interaction of 2–Methoxyestradiol, an Endogenous Mammalian Metabolite, with Umpolymerized Tubulin and with Tubulin Polymers (Abstract only). *Biochemistry*vol./Iss: 35 (4) pp. 1304–1310 1996.

Handley et al. Chronic bullous disease of childhood and ulcerative colitis. *British Journal of Dermatology*vol/Iss: 4(4) pp. 67–68 1994.

He et al. A Versatile Synthesis of 2–Methoxyestradiol, and Endogenous Metabolite of Estradiol which Inhibits Tubulin Polymerization by Binding to the Colchicine Binding Site. *Bioorganic & Medicinal Chemistry Letters*vol/Iss: 4(14) pp. 1724–1728 1994.

He et al. Novel Cytokine Release Inhibitors. Part II Steroids. *Bioorganic & Medicinal Chemistry Letters*vol/Iss; 8 pp. 2805–2828. 1996.

HeJaz et al. Synthesis and Biological Activity of the Superestrogen (E)–17–Oximino–3–O–sulfamoyl–1,3,5(10)–estratriene: X–ray Crystal Structure of (E)–17–Oximino–3–hydroxy–1,3,5(10)–estratriene. *Journal of Medicinal Chemistry*vol/Iss: 42 (16) pp. 3188–3192 1999.

Heney et al. Thalidomide treatment for chronic graft–versus–host disease. *British Journal f Haematology*vol/Iss: 78(1) May 1991.

Holker et al. The Reactions of Estrogen with Benzeneseleninic Anhydride and Hexamethyldisilazane. *J. Chem. Soc. Perkin Trans.*vol/Iss. i 1915–1918 198.

Hori, A. et al. Suppression of Solid Tumor Growth by Immunoneutralizing Monoclonal Antibody Against Human Basic Fibroblasts Growth Factor. *Cancer Research*vol/Iss: 51 6180–6184 Nov. 15, 1991.

Hu, G. Neomycin Inhibits Angiogenin–induced Angiogenesis (Abstract Only). *Proceedings of the National Academy of Sciences, USA*vol./Iss: 10(2) pp. 9791–9795 Apr. 13, 1976.

Ikegawa et al. Immunoaffinity extracts for liquid chromatographic determination of equilin and its metabolites in plasma (Abstract only). vol/Iss: 10(2) pp, 73–77 1996.

Imamura et al. Method for Manufacture of Dihydric Phenols (Abstract only). *USPATFULL 76:20259 US 3,950,437*Apr. 13, 1976.

Ingber, D. et al. Synthetic analogues of fumagillin that inhibit angiogenesis and supports tumor growth *Nature*vol/Iss: 348 PP. 555–557 Dec. 6, 1990.

Iriarte et al. Steroids: (XCIV). Synthesis of 2–methyl and 1,2–dimethyl estrogens (Abstract only). *Tetrahedron*vol./Iss: 3 pp. 28–36. 1958.

Jaggers et al. Inhibitory Effects of Steroids in an in vitro Model of Angiogenesis (Abstract only). *Journal of Endocrinology*vol./Iss: 150 (3) pp. 457–464. 1998.

Jhingran et al. Studies in Antifertility Agents –Part XLI: Secosteroids–x: Synthesis of Various Stereoisomers of (+–)–2, 6β–diethyl–7α–ethynyl–3–(p–hydroxyphenyl)–trans–bicyclo ( 4.3.0) nonan–7β–ol.

Josefsson et al. Suppression of Type II Collagen–Induced Arthritis by the Endogenous Estrogen Metabolite 2–Methoxyestradiol. *Arthritis & Rheumatism*vol./Iss: 40 (1): pp. 154–163 Jan. 1997.

Kabarity et al. Further Investigation on the cytological effects of some contraceptives. *Mutation Research*vol./Iss: 135 pp. 181–188. 1964.

Karwat Separation and Recovery of Hydrogen Sulfide from Hydrocarbon Mixture. *Caplus DE 1103310*Sep. 2, 1959.

Kataoka et al. An agent that Increases Tumors Suppressor Transgene Product Coupled with Systemic Transgene Delivery Inhibits Growth of Metastatic Lung Cancer in Vivo (Abstract only). *Cancer Research*vol./Iss: 58(21) pp. 4761–4765. Nov. 1998.

Kelly et al. The Stimularion of Prostaglandin Production by Two Antiprogesterone Steroids in Human Endometrial Cells (Abstract only). *Journal of Clinical Endocrinology Metabolism*. vol./Iss: 62(6) pp. 1116–1123. Jun. 1966.

Kim, K.J. et al. Inhibition of Vascular Endothelial Growth Factor–Induced Angiogenesis Suppresses Tumor Growth In Vivo. *Nature*vol./Iss: 362 pp. 841–844 Apr. 29, 1993.

Klauber et al. Inhibition of Angiogenesis and Breast Cancer in Mice by the Microtubule Inhibitors 2–Methoxygenated and Taxol. *Cancer Research*vol./Iss: 57 pp. 81–86 Jan. 1, 1997.

Knighton, D. et al. A vascular and Vascular Phases of Tumour Growth in the Chick Embryo. *British Journal of Cancer*vol./Iss: 35 pp. 347–356 1977.

Kole et al. Studies in Antifertility Agents. 11. Secosteroids.5.Synthesis of 9,11–Secoestradiol. *Journal of Medicinal Chemistry*vol./Iss: 18 (7) pp. 765–766 1975.

Kovacs et al. Steroids. XXIII. Synthesis of 2–and 4–hydroxy and 2,4–dihydroxy derivatives of estrone and estradiol (Abstract only). *Acta Phys. Chem.*vol./Iss: 19 (3) pp. 287–290 1973.

Lebras, J. et al. Activation and Regioselective Ortho–Functionalization of the A–Ring of β–Estradiol Promoted by "Cplr": An Efficient Organometallic Procedure for the Synthesis of 2–Methoxyestradiol. *Organometallics*vol./Iss: 16 pp. 1765–1771 1997.

Lewis, Richard J. *Hawley's Condensed Chemical Dictionary*. p. 577 Jan. 1993.

Lewis, Richard J. *Hawley's Condensed Chemical Dictionary*pp.128–129. Jan. 1993.

Li, J., et al. (DN 103:64176) Catechol Formation of Fluoro–and Bromo–substituted Estradiols by Hamster Liver Microsomes. Evidence for Dehalogenation. (Abstract only). *CAPLUS; Molecular Pharmacology*vol./Iss: 27 (5) pp. 559–565 1985.

Lien W. et al. The blood supply of experimental liver metastases. II. A Microcirculatory study of the normal and tumor vessels of the liver with the use of perfused silicone rubber. *Surgery*vol./Iss: 68 (2) pp. 334–340 Aug. 1970.

Limantsev et al. Effect of some estrogen structural analogs on the development of the mouse embryo (Abstract only). *Akush Jinkeol.*vol./Iss: 6 pp. 55–56 1982.

Liu et al. Total Synthesis of (+–)–$\Delta^{9(12)}$–Capnellene. *Tetrahedron Letters*vol./Iss: 26(40) pp. 4847–4850. 1985.

Loozen et al. An approach to the synthesis of 7.beta–amino estrogens (Abstract only). *Recl.: J.R. Neth.Chem. Soc.*vol./Iss: 102(10) pp. 433–437 1983.

Lottering et al. 17β–Estradiol Metabolites Affect Some Regulators of the MF–7 Cell Cycle. *Cancer Letters*vol./Iss: 110 pp. 181–186 1996.

Lovely et al. 2–(Hydroxyalkyl)estradiols: Synthesis and Biological Evaluation. *Journal of Medicinal Chemistry*vol./Iss: 39 pp. 1917–1923 1996.

Luo et al. Effect of Components of Growth Ether Copper(I) Iodide Mixed Catalyst on Nucleophilic Substitution of Bromoestrogen (Abstract No. 195225). *Chemical Abstracts*vol./Iss: 111 (2) p. 818, Column 1 Nov. 20, 1988.

Maro et al. Mechanism of Polar Body Formation in the Mouse Oocyte: An Interaction Between the Chromosomes, the Cytoskeleton and the Plasma Membrane. *Journal of Embryology and Experimental Morphology*vol./Iss: 92 pp. 11–32 1986.

Mayol et al. Ethynylestradiol–Induced Cell Proliferation in Rat Liver Involvement of Specific Population of Hepatocytes (Abstract only). *Carcinogenesis*vol./Iss: 13 (12) 2381–2388 1992.

Meikrantz et al. Apoptosis and the Cell Cycle. *Journal of Cellular Biochemistry*vol./Iss: 58(2) 160–174 Jun. 1995.

Meza et al. Managing the Gastrointestinal Complications of AIDS. *Drug Therapy*vol./Iss: 23 (11) pp. 74–83 Nov. 1993.

Michel et al. Inhibition of synaptosomal high–affinity uptake of dopamine and serotonin by estrogen agonists and antagonists (Abstract only) *Biochem. Pharmacol.*vol/Iss: 36 (19) pp. 3175–3180 1967.

Miller et al. Synthesis and Structure–Activity Profiles of A–Homoestranes, the Estratropones. *Journal of Medicinal Chemistry*vol/Iss: 40 pp. 3836–3841 1997.

Miller, Thomas Tubulin as a Therapeutic Target (Abstract Only). *Dissertations Abstracts International*vol/Iss: 5907B 1998.

Morisaki et al. Steroids: L1. Aromatization reaction of the cross–conjugated dienone system by Zinc. *Chem. Pharm. Bull.*vol./Iss: 14 (8) pp. 866–872 1966.

Mukhopadhyay et al. Induction of Apoptosis in Human Lung Cancer Cells after Wild–Type p53 Activation by Methoxyestradiol. *Oncogene*vol/Iss: 14 pp. 379–384 1997.

Naafs et al. Thalidomide Therapy An Open Trial. *International Journal of Chemistry*vol/Iss: 24 (2) pp. 131–134 Mar. 1985.

Nakagawa–Yagi et al. The Endogenous Estrogen Metabolite 2–Methoxyestradiol Induces Apoptotic Neuronal Cell Death *In Vitro*. *Life Sciences*vol/Iss: 58 (17) pp. 1461–1467 1996.

Nambara et al. Studies on Steroid Conjugates. III. New Synthesis of 2–Methoxyestrogens. *Chem. Pharm. Bulletin*vol/Iss: 18(3) pp. 474–480 Mar. 1970.

Nambara et al. Microbial transformation products derived from steroids. I. Synthesis of 1,2–and 3–dimethoxy–4–methylestratrienes (Abstract only).

Namnara et al. Synthesis of 16β–Oxygenated Catechol Estrogen Methyl Ethers, New and Potential Metabolites. *Chemical & Pharmaceutical Bulletin*vol/Iss: 23 (17) pp. 1613–1616 Jul. 1975.

Nambara, T., et al. DN 82:43650; Analytical Chemical Studies on Steroids. LXXIII. Synthesis of Epimeric 2–Hydroxy–16–Chlorestrong Monomethyl Ethers (Abstract only). *HCAPLUS–Chemical and Pharmaceutical Bulletin*vol/Iss: 22 (10) pp. 2455–2457 1974.

Napolitano et al. 11 Beta–Substituted Estradiol Derivatives. 2 Potential Carbon–11 and Iodine–Labeled Probes for the Estrogen Receptor (Abstract only). *Journal of Medicinal Chemistry*vol/Iss: 38 (14) pp. 2774–2779 Jul. 7, 1995.

Newkome et al. Synthesis of Simple Hydrazones of Carbony Compounds by an Exchange Reaction. *Journal of Organic Chemistry*vol/Iss: 31 pp. 677–681 Mar. 1966.

Nguyen, M. et al. Elevated Levels of the Angiogenic Peptide Basic Fibroblast Growth Factor in Urine of Bladder Cancer Patients. *Journal of the National Cancer Institute*vol./Iss: 85 (3) pp. 241–242 Feb. 3, 1993.

Nishigaki et al. Anti–Proliferative Effect of 2–Methoxyestradiol on Cultured Smooth Muscle Cells from Rabbit Aorta. *Atherosclerosis*vol/Iss: 113 pp. 167–170 1995.

Numazawa et al. Efficient Synthesis of 2–Methoxy–and 4–Metehoxy–Estrogens. *Journal of the Chemical Society*pp. 533–534 Jan. 1, 1983.

Numazawa et al. Novel and Regiospecific Synthesis of 2–Amino Estrogens via Zincke Nitration. *Steroids*vol/Iss: 41 (5) pp. 675–682 1983.

Ochs et al. Effect of Tumor Promoting Contraceptive Steroids on Growth and Drugs Metabolizing Enzymes in Rat Liver (Abstract only). *Cancer Research*vol/Iss: 46 (3) pp. 1224–1232 1986.

Omar et al. Synthesis, binding affinities and uterotrophic activity of some 2–substituted estradiol and ring–A–fused pyrone derivatives. *European Journal of Medicinal Chemsitry*vol/Iss: 29 pp. 25–32 1994.

Parthasarathy et al. A New Role for RU–486 and Related Compounds (Abstract only). *Journal of Clinical Investigation*vol/Iss: 94 (5) pp. 1990–1995 Nov. 1994.

Pert et al. Preparation of 2,4–disubstituted estradiols (Abstract only). *Australian Journal of Chemistry*vol/Iss: 42 (3) pp. 421–432 1989.

Peters et al. 17–Desoxy Estrogen Analogues. *Journal of Medicinal Chemistry*vol/Iss: 32 (7) pp. 1642–1652 1989.

Pfeiffer et al. Are catechol estrogens obligatory mediators of estrogen action in the central nervous system?1. Characterization of pharmacological probes with different receptor binding affinities and catechol estrogen formation rates (Abstract only). *Journal of Endocrinology*vol/Iss: 110 (3) pp. 489–497 1986.

Powell et al. Investigation and Treatment of Orogfenital Ulceration; studies on a Possible Mode of Action of Thalidomide. *British Journal of Dermatology*vol/Iss: 113 Supp. 28 Jul. 1985.

Rao et al. A Novel, Two–Step Synthesis of 2–Mehoxyestradiol. *Synthesis*vol/Iss: pp. 168–169 Mar. 1, 1977.

Romanelli et al. Ethyl–p–Dimethylaminophenylacetate. *Organic Synthesis*vol/Is: 5 p. 552 Oct. 24, 1973.

Sakakibara, Kyoichi 2–Hydroxy–1,3,5(10)–estratriene derivatives (Abstract only) (Identifier: XP–002186126). *Chemical Abstracts*vol/Iss: 60(1) Jan. 6, 1964.

Sato et al. Natural estrogen induce modulation of microtubules in Chinese hamster V79 cells in culture (Abstract only). *Horm. Carconog. II. Proceedings Int. Symp., 2nd (1996), Meeting Date 1994*vol/Iss: pp. 454–457 1996.

Seegers et al. The Mammalian Metabolite, 2–methoxyestradiol, Affects P53 Levels and Apoptosis Induction in Transformed Cells but Not in Normal Cells (Abstract only). *Journal of Steroid Biochemistry and Molecular Biology*vol/Iss: 62(4) pp. 253–267 Jul. 1997.

Shah et al. (+/−)–N–alkylamino)benzazepine Analogs: Novel Dopamine D1 Receptor Antagonists (Abstract only). *Journal of Medicinal Chemistry*vol/Iss: 38(21) pp. 4284–4293. Oct. 13, 1995.

Shishkina et al. Synthesis and properties of condensed heterocyclic derivatives of estra–4, 9–dien–17.beta.–0l–3–one (Abstract only). *Khim.–Farm.Zh.*8(1) pp. 7–11 1974.

Sidky et al. Inhibition of Angiogenesis by Interferons: Effects on Tumor–and Lymphocyte–induced Vascular Responses. *Cancer Research*vol/Iss: 47 pp. 5155–5161 Oct. 1, 1987.

Siracusa et al. The Effect of Microtubule–and Microfilament–disrupting Drugs αPreimplantation Mouse Embryos (abstract Only). *Journal of Embryology and Experimental Morphology*vol/Iss: 60 pp. 71–82 Dec. 1980.

Spyriounis et al. Copper (II) complex of an estradiol derivative with potent antiinflammatory properties (Abstract only). *Arch. Pharm.*vol/Iss: 324 (9) pp. 533–536 1991.

Srivastava, A. et al. The Prognostic Significance of Tumor Vascularity in Intermediate–Thickness (0.76–4.0 mm Thick) Skin Melanoma. *American Journal of Pathology*vol/Iss: 133 (2) pp. 419–424 Nov. 1988.

Starkov et al. Momo–and Dialkylation of Guaiacol by Olefins on KU–2 Cation Exchanger (Abstract only). *Zhumal Prikladnoi Khimii*vol/Iss: 41 (3) pp. 688–690 1968.

Taylor, S. et al. Protamine is an Inhibitor of Angiogenesis. *Nature*vol/Iss: 297 pp. 307–312 May 27, 1982.

Teranishi, M. et al. Methylation of Catechol Estrogen with Diazomthane. *Chemical and Pharmaceutical Bulletin*vol/Iss: 31 (9) pp. 3309–3314 Sep. 1983.

Tishler et al. Microtubule–Active Drug Taxol, Vinblastine, and Nocodazole Increase the Levels of Transcriptionally Active p53. *Cancer Research*vol/Iss: 55 pp. 2483–2495 1995.

Tremblay, et al. A Convenient Synthetic Method for Alpha–Alkylation of Steroidal 17–Ketone: Preparation of 16α–(THPO–Heptyl)–Estradiol. *Synthetic Communications*vol/Iss: 25(16) pp. 2483–2495. 1995.

Tremblay, et al. Synthesis of 16–(Bromoalkyl)–Estradiols Having Inhibitory Effect on Human Placental Estradiol 17β–Hydroxysteroid Dehydrogenase (17βHSD Type 1). *Bioorganic & Medicinal Chemistry*vol/Iss: 3 (5) pp. 505–523 1995.

Utne et al. The Synthesis of 2–and 4–Fuoroestradiol. *Journal of Chemistry*vol/Iss: 33 (6) pp. 2469–2473 Jun. 1968.

Van Geerestein et al. Structure of 11.beta.–(4–dimethylamino)phenyl–17.beta.–hydroxy–17.alpha.–(2–propenyl estra–4,9–dien–3–one (Identifier only). *Acta Crystallogra., Sect. C: Cryst. Struct. Commun.*vol/Iss: C43 (2) pp. 319–322 1987.

Vicente et al. In Vitro Activity of Thalidomide Against *Mycobacterium avium*Complex *Archives of Internal Medicine*vol/Iss: 153 (4) p. 534 Feb. 22. 1993.

Wang et al. Photoaffinity Labeling 6 Human Placental Estradiol 17.beta.–dehydrogenase 2–And 4–azidoestrone, 2–and 4–azidoestrone, 2–and 4–azidoestradiol (abstract Only). *Shengwu Huaxue Zazhi*vol/Iss: 8(6)pp. 715–718 1992.

Wang, Z. et al. An Optimied Synthesis of 2–Methoxyestradiol, a Naturally Occurring Human Metabolite with Anticancer Activity. *Synth. Commun.*vol/Iss: 28 (23) pp. 4431–4437 1998.

Weidner, N. et al. Tumor angiogenesis: A New Significant and Independent Prognostic Indicator in Early–Stage Breast Carcinoma. *Journal of the National Cancer Institute*vol/Iss: 84 pp. 1875–1877 Dec. 16, 1992.

Weidner, N. et al. Tumor Angeiogenesis Correlates with Metastasis in Invasive Prostate Carcinoma. *American Journal of Pathology*vol/Iss: 143 (2) pp. 401–409 Aug. 1, 1993.

Weidner, N. et al. Tumor Angiogenesis and Metastasis–Correlation in Invasive Breast Carcinoma. *New England Journal of Medicine*vol. 324 (1) pp. 1–8 Jan. 1, 1991.

Welsch et al. Staphylostatic Activity of Some New Diphenols, Napthols, and Chalcones (Abstract only). *Experientia-*volIss: 11 pp. 350–351 1955.

White et al. Treatment of Pulmonary Hemangiomatosis with Recombinant Interfron Alfa–2a. *The New England Journal of Medicine*vol/Iss: 32 (18) pp. 1197–1200 May 4, 1989.

Wiese et al. Induction of the Estrogen Specific Mitogenic Response of MCF–7 Cells by Selected Analogues of Estradiol–17 β: A 3D QSAR Study. *Journal of Medicinal Chemistry*vol/Iss: 40 pp. 3659–3669 1997.

Wurtz et al. Three–Dimensional Models of Estrogen Receptor Ligand Binding Domain Complexes Based on Related Crystal Structures and Mutational and Structure–Activity. *Journal of Medicinal Chemistry*vol/Iss: 41 pp. 1803–1814 1998.

Yasuda et al. Accelerated differentiation in eeminiferous tubules of fetal mice prenatally exposed to ethinyl estradiol (Abstract only). *Anat. Embryol. (Berl.)*vol/Iss: 174 (3) pp. 289–299 1986.

Yue et al. 2–Methoxyestradiol, an Endogenous Estrogen Metabolite, Induces Apoptosis in Endothelial Cells and Inhibits Angiogenesis: Possible Role for Stress–Activated Protein Kinase Signaling Pathway and Fas Expression. *Molecular Pharmacology*vol/Iss: 51 pp. 951–962 1997.

\* cited by examiner

ESTROGENIC COMPOUNDS AS ANTI-MITOTIC AGENTS

CROSS-REFERENCE TO RELATED APPLICATIONS

This application is a continuation of application Ser. No. 09/436,610, filed Nov. 9, 1999, now abandoned, which is a continuation of application Ser. No. 09/243,158, filed Feb. 2, 1999, now U.S. Pat. No. 6,528,676, which is a division of application Ser. No. 08/838,699, filed Apr. 25, 1997, now U.S. Pat. No. 5,892,069, which is a division of application Ser. No. 08/571,265 filed Dec. 12, 1995, now U.S. Pat. No. 5,661,143, which is a continuation of application Ser. No. 08/102,767, filed Aug. 6, 1993, now U.S. Pat. No. 5,504,074.

BACKGROUND OF THE INVENTION

This invention relates to treating disease states characterized by abnormal cell mitosis.

Cell mitosis is a multi-step process that includes cell division and replication (Alberts, B. et al. In The Cell, pp. 652–661 (1989); Stryer, E. *Biochemistry* (1988)). Mitosis is characterized by the intracellular movement and segregation of organelles, including mitotic spindles and chromosomes. Organelle movement and segregation are facilitated by the polymerization of the cell protein tubulin. Microtubules are formed from α and β tubulin polymerization and the hydrolysis of GTP. Microtubule formation is important for cell mitosis, cell locomotion, and the movement of highly specialized cell structures such as cilia and flagella.

Microtubules are extremely labile structures that are sensitive to a variety of chemically unrelated anti-mitotic drugs. For example, colchicine and nocadazole are anti-mitotic drugs that bind tubulin and inhibit tubulin polymerization (Stryer, E. *Biochemistry* (1988)). When used alone or in combination with other therapeutic drugs, colchicine may be used to treat cancer (WO-9303729-A, published Mar. 4, 1993; J03240726-A, published Oct. 28, 1991), alter neuromuscular function, change blood pressure, increase sensitivity to compounds affecting sympathetic neuron function, depress respiration, and relieve gout (*Physician's Desk Reference*, Vol. 47, p. 1487, (1993)).

Estradiol and estradiol metabolites such as 2-methoxyestradiol have been reported to inhibit cell division (Seegers, J. C. et al. *J. Steroid Biochem.* 32, 797–809 (1989); Lottering, M-L. et al. *Cancer Res.* 52, 5926–5923 (1992); Spicer, L. J. and Hammond, J. M. *Rol. and Cell. Endo.* 64, 119–126 (1989); Rao, P. N. and Engelberg, *J. Exp. Cell Res.* 48, 71–81 (1967)). However, the activity is variable and depends on a number of in vitro conditions. For example, estradiol inhibits cell division and tubulin polymerization in some in vitro settings (Spicer, L. J. and Hammond, J. M. *Mol. and Cell. Endo.* 64,-119-126 (1989); Ravindra, R., *J. Indian Sci.* 64(c) (1983)), but not in others (Lottering, M-L. et al. *Cancer Res.* 52, 5926–5923 (1992); Ravindra, R., *J. Indian Sci.* 64(c) (1983)). Estradiol metabolites such as 2-methoxyestradiol will inhibit cell division in selected in vitro settings depending on whether the cell culture additive phenol red is present and to what extent cells have been exposed to estrogen. (Seegers, J. C. et al. Joint NCI-IST Symposium. Biology and Therapy of Breast Cancer. 9/25-9/27, 1989, Genoa, Italy, Abstract A58).

Numerous diseases are characterized by abnormal cell mitosis. For example, uncontrolled cell mitosis is a hallmark of cancer. In addition, cell mitosis is important for the normal development of the embryo, formation of the corpus luteum, wound healing, inflammatory and immune responses, angiogenesis and angiogenesis related diseases.

SUMMARY OF THE INVENTION

I have discovered that certain compounds within the scope of the general formulae set forth below in the claims are useful for treating mammalian diseases characterized by undesired cell mitosis. Without wishing to bind myself to any particular theory, such compounds generally inhibit microtuble formation and tubulin polymerization and/or depolymerization. Compounds within the general formulae having said inhibiting-activity are preferred. Preferred compositions may also exhibit a change (increase or decrease) in estrogen receptor binding, improved absorbtion, transport (e.g. through blood-brain barrier and cellular membranes), biological stability, or decreased toxicity. I have also discovered certain compounds useful in the method, as described by the general formulae of the claims.

A mammalian disease characterized by undesirable cell mitosis, as defined herein, includes but is not limited to excessive or abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neovascular glaucoma and Osler Weber syndrome. Other undesired angiogenesis involves normal processes including ovulation and implantation of a blastula. Accordingly, the compositions described above can be used to block ovulation and implantation of a blastula or to block menstruation (induce amenorrhea).

The bond indicated by C..C is absent or, in combination with the C---C bond is the unit HC═CH.

Other features and advantages of the invention will be apparent from the following description of preferred embodiments thereof.

DESCRIPTION OF THE PREFERRED EMBODIMENTS

The drawings are first described.

COMPOUNDS ACCORDING TO THE INVENTION

As described below, compounds that are useful in accordance with the invention include novel estradiol derivatives that bind tubulin, inhibit microtubule formation or exhibit anti-mitotic properties. Specific compounds according to the invention are described below. Those skilled in the art will appreciate that the invention extends to other compounds within the formulae given in the claims below, having the described characteristics. These characteristics can be determined for each test compound using the assays detailed below and elsewhere in the literature.

Figure 3:
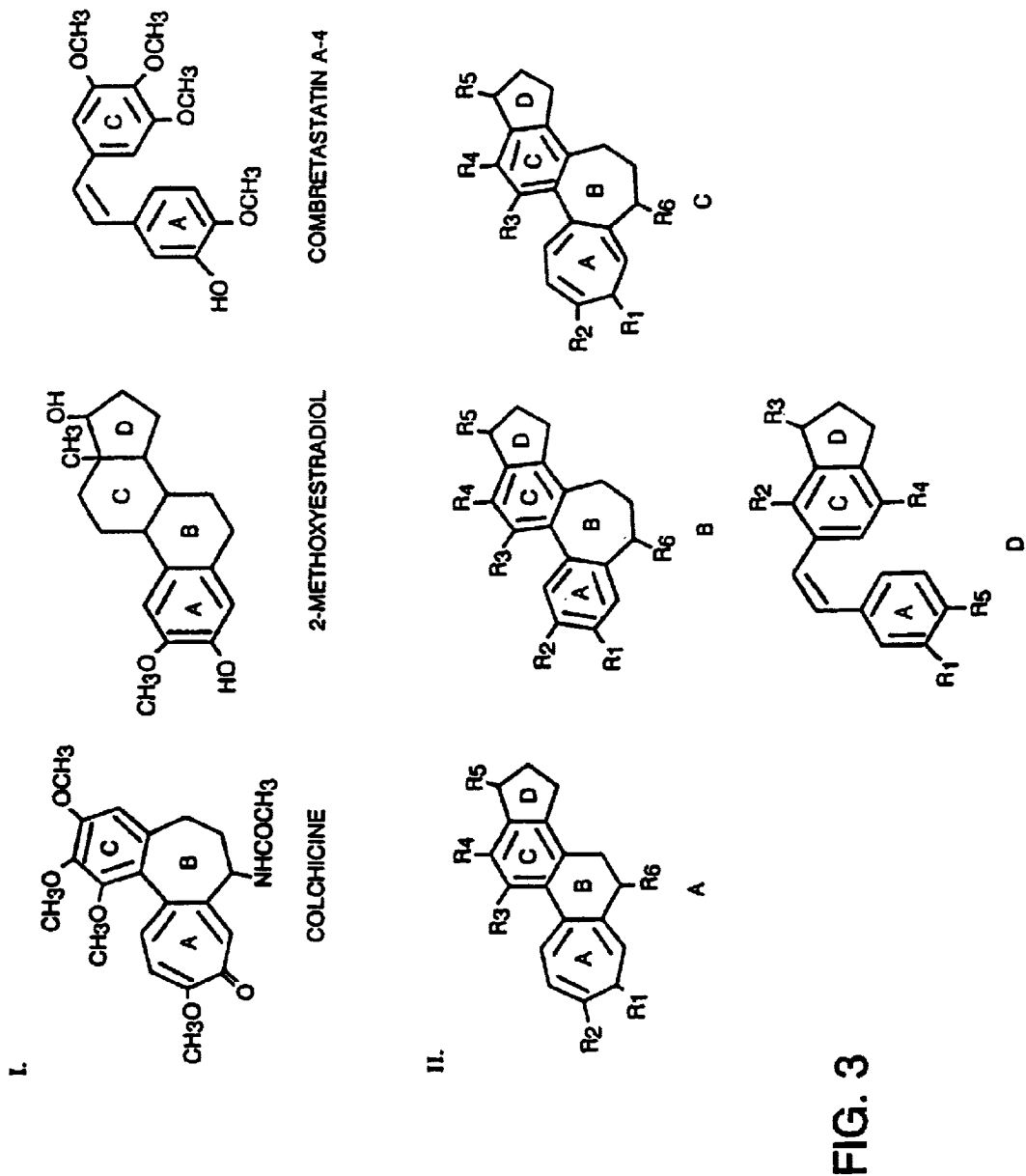
FIG. 3 depicts: I. colchicine, 2-methoxyestradiol and combretastatin A-4, and II. various estradiol derivatives comprising colchicine (a-c) or combretastatin A-4 (d) structural motifs as described below.

Without wishing to bind myself to specific mechanisms or theory, it appears that certain compounds that are known to inhibit microtubule formation, bind tubulin and exhibit anti-mitotic properties such as colchicine and combretastatin A-4 share certain structural similarities with estradiol. FIG. 3 illustrates the molecular formulae of estradiol, colchicine, combretastatin A-4, and improved estradiol derivatives that bind tubulin inhibit microtubule assembly and exhibit antimitotic properties. Molecular formulae are drawn and oriented to emphasize structural similarities between the ring structures of colchicine, combretastatin A-4, estradiol, and certain estradiol derivatives. Estradiol derivatives are made by incorporating colchicine or combretastatin A-4 structural motifs into the steroidal backbone of estradiol.

FIG. 3, part I, depicts the chemical formulae of colchicine, 2-methoxyestradiol and combretastatin A-4. FIG. 3, part IIa-d, illustrates estradiol derivatives that comprise structural motifs found in colchicine or combretastatin A-4. For example, part II a-c shows estradiol derivatives with an A and/or B ring expanded from six to seven carbons as found in colchicine and part IId depicts an estradiol derivative with a partial B ring as found in combretastatin A-4. Each C ring of an estradiol derivative, including those shown in FIG. 3, may be fully saturated as found in 2-methoxyestradiol. $R_{1-6}$ represent a subset of the substitution groups found in the claims. Each $R_1 \rightarrow R_6$ can independently be defined as —$R_1$, $OR_1$, —$OCOR_1$, —$SR_1$, —F, —$NHR_2$, —Br, —I, or —C≡CH.

Anti-mitotic Activity In Situ

Anti-mitotic activity is evaluated in situ by testing the ability of an improved estradiol derivative to inhibit the proliferation of new blood vessel cells (angiogenesis). A suitable assay is the chick embryo chorioallantoic membrane (CAM) assay described by Crum et al. *Science* 230:1375 (1985). See also, U.S. Pat. No. 5,001,116, hereby incorporated by reference, which describes the CAM assay. Briefly, fertilized chick embryos are removed from their shell on day 3 or 4, and a methylcellulose disc containing the drug is implanted on the chorioallantoic membrane. The embryos are examined 48 hours later and, if a clear avascular zone appears around the methylcellulose disc, the diameter of that zone is measured. Using this assay, a 100 mg disk of the estradiol derivative 2-methoxyestradiol was found to inhibit cell mitosis and the growth of new blood vessels after 48 hours. This result indicates that the anti-mitotic action of 2-methoxyestradiol can inhibit cell mitosis and angiogenesis.

Anti-Mitotic Activity In Vitro

Anti-mitotic activity can be evaluated by testing the ability of an estradiol derivative to inhibit tubulin polymerization and microtubule assembly in vitro.

Microtubule assembly is followed in a Gilford recording spectrophotometer (model 250 or 2400S) equipped with electronic temperature controllers. A reaction mixture (all concentrations refer to a final reaction volume of 0.25 μl) contains 1.0M monosodium glutamate (ph 6.6), 1.0 mg/ml (10 μM) tubulin, 1.0 M $Mgcl_2$, 4% (v/v) dimethylsulfoxide and 20–75 μM of a composition to be tested. The 0.24 ml reaction mixtures are incubated for 15 miii. at 37° C. and then chilled on ice. After addition of 10 μl 2.5 mM GTP, the reaction mixture is transferred to a cuvette at 0°C., and a baseline established. At time zero, the temperature controller of the spectrophotometer is set at 37° C. Microtubule assembly is evaluated by increased turbity at 350 nm. Alternatively, inhibition of microtubule assembly can be followed by transmission electron microscopy as described in Example 2 below.

Indications

The invention can be used to treat any disease characterized by abnormal cell mitosis. Such diseases include, but are not limited to: abnormal stimulation of endothelial cells (e.g., atherosclerosis), solid tumors and tumor metastasis, benign tumors, for example, hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying: rheumatoid arthritis, psoriasis, diabetic retinopathy, and other ocular angiogenic diseases such as retinopathy of prematurity (retrolental fibroplasic), macular degeneration, corneal graft rejection, neuroscular glacoma and Oster Webber syndrome.

Improved Estradiol Derivative Synthesis

Known compounds that are used in accordance with the invention and precursors to novel compounds according to the invention can be purchased, e.g., from Sigma Chemical Co., St. Louis, Steroloids and Research Plus. Other compounds according to the invention can be synthesized according to known methods from publicly available precursors.

The chemical synthesis of estradiol has been described (Eder, V. et al., Ber 109, 2948 (1976); Oppolzer, D. A. and Roberts, D. A. *Hely. Chim. Acta.* 63, 1703, (1980)). Synthetic methods for making seven-membered rings in multicyclic compounds are known (Nakamuru, T. et al. *Chem. Pharm. Bull.* 10, 281 (1962); Sunagawa, G. et al. *Chem. Pharm. Bull.* 9, 81 (1961); Van Tamelen, E. E. et al. Tetrahedran 14, 8–34 (1961); Evans, D. E. et al. *JACS* 103, 5813 (1981)). Those skilled in the art will appreciate that the chemical synthesis of estradiol can be modified to include 7-membered rings by making appropriate changes to the starting materials, so that ring closure yields seven-membered rings. Estradiol or estradiol derivatives can be modified to include appropriate chemical side groups according to the invention by known chemical methods (The Merck index, 11th Ed., Merck & Co., Inc., Rahway, N.J. USA (1989), pp. 583–584).

Administration

The compositions described above can be provided as physiologically acceptable formulations using known techniques, and these formulations can be administered by standard routes. In general, the combinations may be administered by the topical, oral, rectal or parenteral (e.g., intravenous, subcutaneous or intramuscular) route. In addition, the combinations may be incorporated into biodegradable polymers allowing for sustained release, the polymers being implanted in the vicinity of where delivery is desired, for example, at the site of a tumor. The biodegradable polymers and their use are described in detail in Brem et al., *J. Neurosurg.* 74:441–446 (1991).

The dosage of the composition will depend on the condition being treated, the particular derivative used, and other clinical factors such as weight and condition of the patient and the route of administration of the compound. However, for oral administration to humans, a dosage of 0.01 to 100 mg/kg/day, preferably 0.01–1 mg/kg/day, is generally sufficient.

The formulations include those suitable for oral, rectal, nasal, topical (including buccal and sublingual), vaginal or parenteral (including subcutaneous, intramuscular, intravenous, intradermal, intraocular, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tables may be made by molding, in a suitable machine, a mixture of the powdered compound moistened with an inert liquid diluent. The tablets may optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tables of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of this invention may include other agents convention in the art having regard to the type of formulation in question, for example, those suitable for oral administration may include flavoring agents.

EXAMPLE 1

Figure 1:
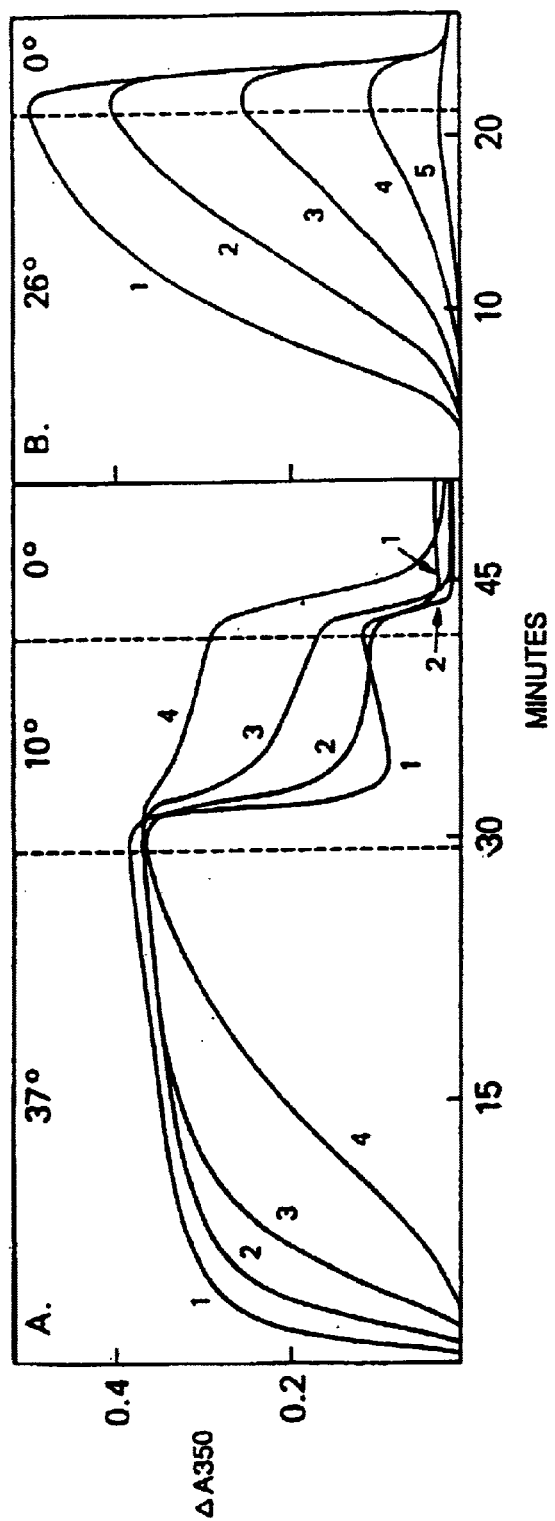
FIG. 1 is a graph illustrating the inhibition of tubulin polymerization by 2-methoxyestradiol described by Example 1 below.

FIG. 1 illustrates the inhibition of tubulin polymerization by 2-methoxyestradiol.

A. Each reaction mixture (all concentrations refer to the final reaction volume of 0.25 ml) contained 1.0 M monosodium glutamate (pH 6.6), 1.0 mg/ml (10 µM) tubulin, 1.0 mM $MGCl_2$, 4% (v/v) dimethylsulfoxide, and either 0 (curve 1), 20 µM (curve 2), 40 µM (curve 3), or 75 µM (curve 4) 2-methoxyestradiol. The 0.24 ml reaction mixtures were incubated for 15 min at 37° C. and chilled on ice. After addition of 10 µl of 2.5 mM GTP the reaction mixtures were transferred to cuvettes held at 0° C., and baselines were established. At time zero the temperature controller was set at 37° C. At the times indicated by the vertical dashed lines the temperature controller was set at the indicated temperatures.

B. Each reaction mixture contained 0.8 M monosodium glutamate (pH 6.6), 1.2 mg/ml (12 µM) tubulin, 4% (v/v) dimethylsulfoxide, and either 0 (curve 1), 1.0 µM (curve 2), 2.0 µM (curve 3), 3.0 µM (curve 4), or 4.0 µM (curve 5) 2-methoxyestradiol. The 0.24 ml reaction mixtures were incubated for 15 min at 26° C. and chilled on ice. After addition of 10 µl of 10 mM GTP the reaction mixtures were transferred to cuvettes held at 0° C., and baselines were established. At time zero the temperature controller was set at 26° C. At the time indicated by vertical dashed line the temperature controller was set at 0° C.

EXAMPLE 2

Transmission electron microscopy (TEM) can show differences between the morphology of polymerized tubulin formed in the absence or presence of 2-methoxyestradiol. After a 30 min incubation (37° C.) of reaction mixtures containing the components described in Example 1, 75 µM 2-methoxyestradiol was added, and aliquots were placed on 200-mesh carbon coated copper grids and stained with 0.5% (w/v) uranyl acetate. TEM magnifications from 23,100× to 115,400× were used to visualize differences in tubulin morphology.

EXAMPLE 3

Figure 2:
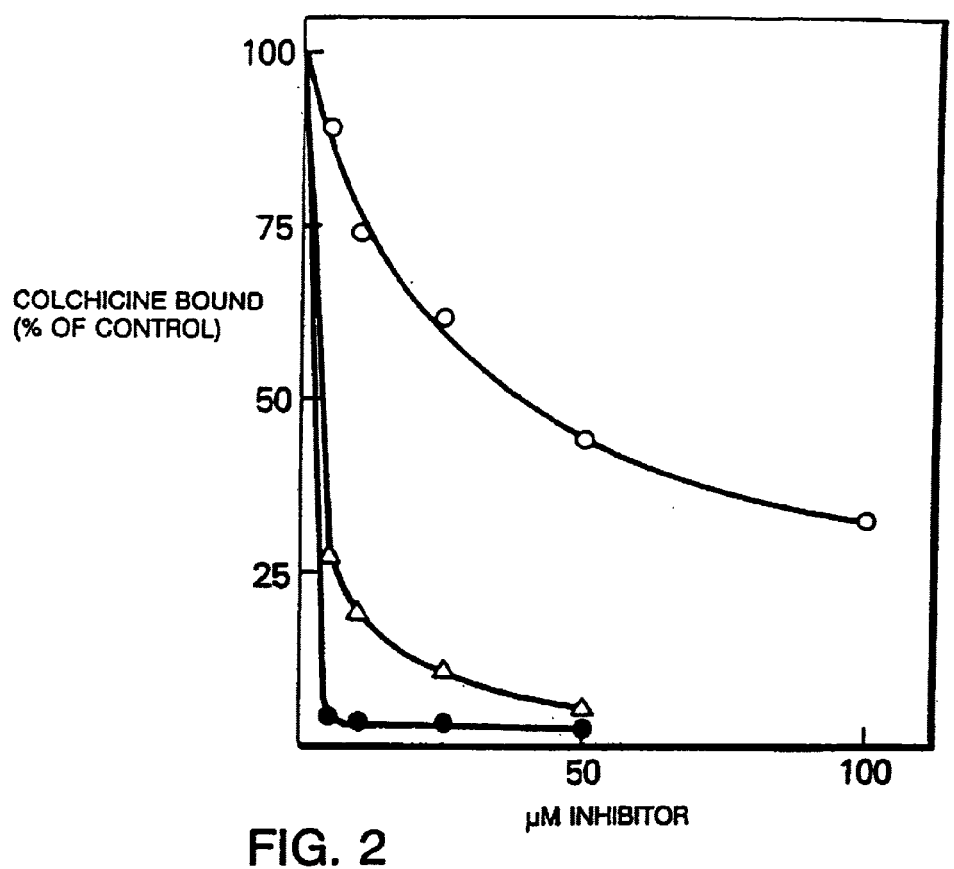
FIG. 2 is a graph illustrating the inhibition of colchicine binding to tubulin by 2-methoxyestradiol described by Example 2 below.

FIG. 2 illustrates that 2-methoxyestradiol inhibits colchicine binding to tubulin. Reaction conditions were as described in the text, with each reaction mixture containing 1.0 pM tubulin, 5% (v/v) dimethyl sulfoxide, 5 pM [$^3$H] colchicine, and inhibitor at the indicated concentrations.

Incubation was for 10 min at 37° C. Symbols as follows: ○, 2-methoxyestradiol; ●, combretastatin A-4; Δ, dihydrocombretastatin A-4. Combretastatin A-4 and dihydrocombretastatin A-4 are compounds with anti-mitotic activity similar to colchicine.

EXAMPLE 4

Table 1 illustrates the inhibitory effects on tubulin polymerization in vitro exhibited by estradiol or estradiol derivatives, plant anti-mitotic compounds such as colchicine, combretastatin A-4 or other plant compounds. The method is given in Example 1.

EXAMPLE 5

Table 2 lists estrogens, estradiol or estradiol derivatives that inhibit colchicine binding to tubulin, by the method given in Example 3.

TABLE 1

| Estrogenic Compound | $IC_{50}$ (μM ± S.D.) |
| --- | --- |
| 2-Methoxyestradiol | 1.9 ± 0.2 |
| Diethylstilbestrol | 2.4 ± 0.4 |
| 2-Bromoestradiol | 4.5 ± 0.6 |
| 2-Methoxyestrone | 8.8 ± 1 |
| 17-Ethynylestradiol | 10.0 ± 2 |
| 2-Fluoroestradiol | 27.0 ± 6 |
| Estradiol | 30.0 ± 6 |
| Estrone | >40 |
| 2-Methoxy-17-ethynylestradiol | >40 |
| Estriol | >40 |
| 2-Methoxyestriol | >40 |
| Estradiol-3-O-methyl ether | >40 |
| 2-Methoxyestradiol-3-O-methyl ether | >40 |
| 4-Methoxyestradiol | >40 |
| 4-Methoxyestradiol-3-O-methyl ether | >40 |
| Plant Products | |
| Colchicine | 0.80 ± 0.07 |
| Podophyllotoxin | 0.46 ± 0.02 |
| Combretastatin A-4 | 0.53 ± 0.05 |
| Dihydrocombretastatin A-4 | 0.63 ± 0.03 |

$IC_{50}$ values are defined as the concentration of an estradiol derivative required to inhibit tubulin polymerization by 50%. $IC_{50}$ values were obtained in at least two independent experiments for non-inhibitory agents ($IC_{50}$>40 μM) and at least three independent experiments for inhibitory compounds. $IC_{50}$ values were obtained graphically, and average values are presented. S.D., standard deviation.

TABLE 2

| Estrogenic Compound | Percent inhibition ± S.D. |
| --- | --- |
| 2-Methoxyestradiol | 82 ± 2 |
| 2-Methoxyestrone | 57 ± 6 |
| 17-Ethynylestradiol | 50 ± 7 |
| Estradiol | 38 ± 4 |
| Diethylstilbestrol | 30 ± 4 |

Reaction conditions were described in Example 3, with each reaction mixture containing 1.01M tubulin, 5% (v/v) dimethyl sulfoxide, 2 μM [$^3$H]colchicine, and 100 μM inhibitor. Incubation was for 10 min at 37° C. Average values obtained in three independent experiments are presented in the table, except for 2-methoxyestrone, which was only examined twice. S.D., standard deviation.

What is claimed is:

1. A method for treating atherosclerosis in a human or animal comprising administering to the human or animal a composition comprising an effective angiogenesis-inhibiting amount of 2-methoxyestradiol.

2. A method for treating tumors in a human comprising administering to the human a composition comprising an effective angiogenesis-inhibiting amount of 2-methoxyestradiol, wherein the tumors are solid tumors, benign tumors, or metastatic tumors.

3. The method of claim 2, wherein the tumors are solid tumors.

4. The method of claim 2, wherein the tumors are benign tumors.

5. The method of claim 2, wherein the tumors are metastatic tumors.

6. The method of claim 4, wherein the benign tumors are selected from hemangiomas, acoustic neuromas, neurofibromas, trachomas, or pyogenic granulomas.

7. A method for treating nerve cell diseases in a human or animal comprising administering to the human or animal with the nerve cell disease a composition comprising an effective angiogenesis-inhibiting amount of 2-methoxyestradiol, wherein the nerve cell disease is selected from acoustic neuroma or neurofibroma.

8. A method for treating diseases of the eye in a human or animal comprising administering to the human or animal with a disease of the eye a composition comprising an effective angiogenesis-inhibiting amount of 2-methoxyestradiol, wherein the disease of the eye is selected from trachomas, retinopathy of prematurity, diabetic retinopathy, retrolental fibroplasic, macular degeneration, corneal graft rejection or neovascular glaucoma.

9. A method for treating inflammation in a human or animal comprising administering to the human or animal with inflammation a composition comprising an angiogenesis-inhibiting amount of 2-methoxyestradiol.

10. The method of claim 9, wherein the inflammation is associated with pyogenic granulomas, vascular malfunctions, abnormal wound healing, inflammatory disorders, gout, gouty arthritis, rheumatoid arthritis, psoriasis or immune disorders.

11. A method for treating Behcet's syndrome in a human comprising administering to the human with Belicet's syndrome a composition comprising an effective angiogenesis-inhibiting amount of 2-methoxyestradiol.

12. A method for treating Osler-Weber syndrome in a human comprising administering to the human with Osler-Weber syndrome a composition comprising an effective angiogenesis-inhibiting amount of 2-methoxyestradiol.

13. A method of treating undesired angiogenesis associated with ovulation, implantation of a blastula, or menstruation in a human or animal comprising administering to the human or animal a composition comprising an effective angiogenesis-inhibiting amount to 2-methoxyestradiol.

14. A method of inhibiting excessive or abnormal stimulation of endothelial cells in a human or an animal comprising administering to the human or animal a composition comprising an effective angiogenesis-inhibiting amount to 2-methoxyestradiol.

* * * * *